United States Patent [19]

Perronnet et al.

[11] 3,983,129

[45] Sept. 28, 1976

[54] CERTAIN ISOTHIAZOLOL ESTERS OF PHOSPHORUS ACIDS

[75] Inventors: Jacques Perronnet, Paris; Laurent Taliani, Les Pavillons-sous-Bois; Pierre Girault, Paris; André Poittevin, Vaires-sur-Marne, all of France

[73] Assignee: Roussel-UCLAF, Paris, France

[22] Filed: Jan. 13, 1975

[21] Appl. No.: 540,381

Related U.S. Application Data

[63] Continuation-in-part of Ser. No. 357,820, May 7, 1973, abandoned.

[30] Foreign Application Priority Data

Oct. 11, 1974 France ............................. 74.34267
May 17, 1972 France ............................. 72.17578

[52] U.S. Cl. ..................... 260/302 E; 260/306.8 A; 424/270
[51] Int. Cl.² ....................................... C07D 261/12
[58] Field of Search ................. 260/302 E, 306.8 A Primary Examiner—Richard J. Gallagher
Attorney, Agent, or Firm—Hammond & Littell

[57] ABSTRACT

Novel 3-phosphoryloxy-isothiazoles of the formula

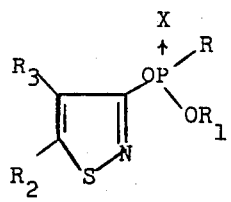

wherein R is selected from the group consisting of alkyl of 1 to 3 carbon atoms, alkoxy of 1 to 3 carbon atoms and

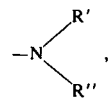

R' and R'' being individually selected from the group consisting of hydrogen and alkyl of 1 to 3 carbon atoms, $R_1$ is alkyl of 1 to 3 carbon atoms, $R_2$ is selected from the group consisting of hydrogen, alkyl of 1 to 5 carbon atoms, aryl of 6 to 10 carbon atoms, aralkyl of 7 to 12 carbon atoms, cyano, carbalkoxy of 2 to 4 carbon atoms and NHR''', and R''' is selected from the group consisting of hydrogen and aryl of 6 to 10 carbon atoms, $R_3$ is selected from the group consisting of cyano, alkylthio of 1 to 4 carbon atoms, alkylsulfinyl of 1 to 4 carbon atoms, alkylsulfonyl of 1 to 4 carbon atoms, carbamoyl, carbalkoxy of 2 to 4 carbon atoms and

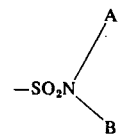

A and B are individually selected from the group consisting of hydrogen and alkyl of 1 to 3 carbon atoms and X is selected from the group consisting of oxygen and sulfur which have excellent insecticidal properties.

13 Claims, No Drawings

CERTAIN ISOTHIAZOLOL ESTERS OF PHOSPHORUS ACIDS

PRIOR APPLICATION

This application is a continuation-in-part of our commonly assigned, copending application Ser. No. 357,820 filed May 7, 1973 now abandoned.

OBJECTS OF THE INVENTION

It is an object of the invention to provide the novel isothiazole derivatives of formula I.

It is another object of the invention to provide a novel process for the preparation of the isothiazoles of formula I.

It is a further object of the invention to provide novel insecticidal compositions and a novel method of combatting insects.

These and other objects and advantages of the invention will become obvious from the following detailed description.

The novel isothiazole derivatives of the invention have the formula

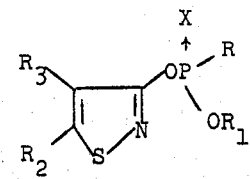

wherein R is selected from the group consisting of alkyl of 1 to 3 carbon atoms, alkoxy of 1 to 3 carbon atoms and

R' and R'' being individually selected from the group consisting of hydrogen and alkyl of 1 to 3 carbon atoms, $R_1$ is alkyl of 1 to 3 carbon atoms, $R_2$ is selected from the group consisting of hydrogen, alkyl of 1 to 5 carbon atoms, aryl of 6 to 10 carbon atoms, aralkyl of 7 to 12 carbon atoms, cyano, carbalkoxy of 2 to 4 carbon atoms and NHR''', R''' is selected from the group consisting of hydrogen and aryl of 6 to 10 carbon atoms, $R_3$ is selected from the group consisting of cyano, alkylthio of 1 to 4 carbon atoms, alkylsulfinyl of 1 to 4 carbon atoms, alkylsulfonyl of 1 to 4 carbon atoms, carbamoyl, carbalkoxy of 2 to 4 carbon atoms and

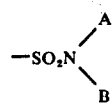

A and B are individually selected from the group consisting of hydrogen and alkyl of 1 to 3 carbon atoms and X is selected from the group consisting of oxygen and sulfur.

Among the preferred compounds of formula I are those where $R_2$ is selected from the group consisting of hydrogen, alkyl of 1 to 3 carbon atoms, aryl of 6 to 10 carbon atoms such as phenyl or naphthyl, arylalkyl of 7 to 12 carbon atoms such as benzyl or phenethyl, cyano, carbalkoxy of 2 to 4 carbon atoms or NHR'''' where R'''' is selected from the group consisting of hydrogen and aryl of 6 to 10 carbon atoms and those where $R_3$ is carbalkoxy of 2 to 4 carbon atoms such as methoxycarbonyl or ethoxycarbonyl. Alkyl is intended to mean straight or branded chain alkyl.

The novel process for the preparation of compounds of formula I comprises reacting a 3-hydroxy-isothiazole of the formula

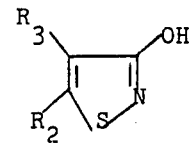

or an alkali metal salt thereof wherein $R_2$ and $R_3$ have the above definition with an halide of a phosphoric or thiophosphoric acid ester of the formula

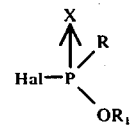

wherein X, R and $R_1$ have the above definitions and Hal is chlorine or bromine to form the corresponding compound of formula I.

The alkali metal salt of the 3-hydroxy-isothiazole of formula II may be sodium, potassium or lithium salt and can be formed by reacting the said 3-hydroxy-isothiazole with an alkali metal hydride, for example.

The reaction to form the compounds of formula I notably takes place in a basic medium in the presence of an organic solvent at a temperature of 0° to 120°C. The base may be an amine or an alkali metal or alkaline earth metal carbonate such as potassium carbonate or sodium carbonate. The organic solvent used may be a hydrocarbon such as benzene, halogenated hydrocarbon such as chloroform, a ketone such as acetone, an ether such as ethyl ether or tetrahydrofuran or other solvents such as dimethylformamide or acetonitrile.

The 3-hydroxy-isothiazoles of formula II used as starting materials can be prepared by a method analogous to that described in French Pat. No. 2,060,868 or by other known methods.

The novel insecticidal compositions of the invention are comprised of an insectidically effective amount of at least one compound of formula I and a carrier. The compositions may be in the form of powders, granules, suspensions, emulsions or solutions containing the compounds of formula I. The compositions may contain cationic, anionic or nonionic surface active agents; inert powders such as talc, clays, silicates or kieselguhr; a vehicle such as water, alcohol, hydrocarbons, other organic solvents, animal, vegetable or mineral oils, etc. The compositions may also contain one or more other active agents.

The compositions possess remarkable insecticidal and/or acaricidal properties and can be used in agriculture to combat harmful organisms such as insects and/or acariens. They are particularly useful or combatting insects which attack stored grains.

The compositions have a very low toxicity to warmblooded animals. For example, 3-(dimethoxythiophosphoryloxy)-4-cyano-5-methyl-isothiazole has a $DL_{50}$ on mice of 1000 to 1500 mg/kg and 3-(dimethoxythiophosporyloxy)-4-cyano-5-n-butyl-isothiazole has a $DL_{50}$ on mice of about 150 mg/kg.

The novel method of the invention of combatting insects and acariens comprises contacting insects or acariens with a lethal amount of at least one compound of formula I.

In the following examples there are described several preferred embodiments to illustrate the invention. However, it is to be understood that the invention is not intended to be limited to the specific embodiments.

EXAMPLE 1

3-(diethoxy thiophosphoryloxy)-4-cyano-5-methyl-isothiazole

STEP A: 3-hydroxy-4-cyano-5-methyl-isothiazole 100 ml of 110 volume hydrogen peroxide were added with stirring to 1000 ml of an aqueous solution of 1M sodium 1,1-dicyano-2-thio-1-propylenate [prepared by method of Hartke, Ang 6, Vol. 83 (1967) ed. Intern] cooled to 10°C and after stirring for 30 minutes, the mixture was acidified to a pH of 1 with concentrated hydrochloric acid. The precipitate formed was recovered by vacuum filtration and was washed with water to obtain 95 g of 3-hydroxy-4-cyano-5-methyl-isothiazole melting at 205°C. Crystallization of the product from ethyl acetate gave a melting point of 209°C.

STEP B: 3-(diethoxy thiophosphoryloxy)-4-cyano-5-methyl-isothiazole

A mixture of 34.5 g of anhydrous potassium carbonate in a solution of 36 g of 3-hydroxy-4-cyano-5-methyl-isothiazole in 1000 ml of acetone was stirred for 10 minutes and then 47 g of 0,0-diethyl chlorothiphosphate were added thereto. The mixture was stirred for 16 hours and the precipitate formed was removed by filtration. The filtrate was evaporated to dryness under reduced pressure at a temperature below 50°C to obtain 75 g of a brown oil which was chromatographed over silica gel (7:3 cyclohexone-ethyl acetate eluant) to obtain 29.7 g of 3-(diethoxy thiophosphoryloxy)-4-cyano-5-methyl-isothiazole in the form of white crystals melting at 35°C.

Analysis: $C_9H_{13}N_2O_3PS_2$; molecular weight = 292.3
Calculated: %C 36.98 %H 4.48 %N 9.58 %P 10.60;
Found: 37.1 4.7 9.6 10.6.

EXAMPLE 2

3-(dimethoxy thiophosphoryloxy)-4-cyano-5-methyl-isothiazole

A mixture of 26.2 g of anhydrous potassium carbonate in a solution of 26.7 g of 3-hydroxy-4-cyano-5methyl-isothiazole in 250 ml of acetonitrile was stirred for 10 minutes and 32.5 g of 0,0-dimethyl chlorothiophosphate were added thereto. The suspension was stirred for 5 hours and the precipitate formed was filtered off. The filtrate was evaporated to dryness under reduced pressure at a temperature below 50°C to obtain 50 g of a brown oil which was chromatographed over silica gel (8-2 benzene-ethyl acetate eluant). The oil obtained was crystallized upon cooling and the crystals were empasted with petroleum ether (B.p. = 35°-70°C) to obtain 32.5 g of 3-(dimethoxy thiophosphoryloxy)-4-cyano-5-methyl-isothiazole melting at 52°C.

Analysis: $C_7H_9N_2O_3PS_2$; molecular weight = 264.2
Calculated: %C 31.82 %H 3.43 %N 10.60 %P 11.72
Found: 31.9 3.5 10.7 11.6

EXAMPLE 3

3-(diethoxy thiophosphoryloxy)-4-carbamoyl-5-methyl-isothiazole

STEP A: 3-hydrox-4-carbamoyl-5-methyl-isothiazole

A mixture of 60 g of 3-hydrox-4-cyano-5-methyl-isothiazole and 150 ml of concentrated sulfuric acid (d = 1.838) was heated for 15 minutes at 113°C and after allowing the temperature to return to 45°C, the mixture was added to ice with stirring. The precipitate formed was recovered by vacuum filtration, was washed with water and then with acetone and dried to obtain 51.5 g of 3-hydroxy-4-carbamoyl-5-methyl-isothiazole melting at 248°-250°C.

STEP B: 3-(diethoxy thiophosphoryloxy)-4-carbamoyl-5-methyl-isothiazole 7.5 g of sodium hydride in 50% mineral oil was added with stirring at a temperature below 45°C to a solution of 25 g of 3-hydroxy-4-carbamoyl-5-methyl-isothiazole in 300 ml of dimethylformamide and the mixture was slowly heated to 140°C and then was cooled. 29.7 g of 0,0-diethyl chlorothiophosphate were added thereto at 15° to 20°C with stirring and the mixture was stirred overnight at room temperature. The mixture was evaporated to dryness under reduced pressure and the residue was taken up in ether. The ether solution was filtered to remove mineral salts and the filtrate was evaporated to dryness to obtain an oil which was chromatographed over silica gel (eluant: 7-3 benzene-acetone) to obtain 35 g of 3-(diethoxy thiophosphoryloxy)-4-carbamoyl-5-methyl-isothiazole melting at 68°C.

Analysis: $C_9H_{15}N_2O_4PS_2$; moleculare weight = 310.33
Calculated: % C 34.83 % H 4.87 % N 9.03 % P 9.98
Found: 35.1 5.1 8.7 9.9

EXAMPLE 4

3-(dimethoxy thiophosphoryloxy)-4-carbamoyl-5-methyl-isothiazole 7.5 g of sodium hydride in 50% mineral oil mixture were added with stirring at a temperature below 45°C to a solution of 25 g of 3-hydroxy-4-carbamoyl-5-methyl-isothiazole in 300 ml of dimethylformamide and the mixture was slowly heated to 140°C and held there for 5 minutes. After cooling the mixture to 20°C, 25.3 g of 0,0-dimethyl chlorothiophosphate were added with stirring and the mixture was stirred for 3 hours at room temperature. The organic phase was evaporated to dryness and the residue was chromatographed over silica gel and eluted with 7-3 benzene-acetone mixture to obtain 20 g of 3-(dimethoxy thiophosphoryloxy)-4-carbamoyl-5-methyl-isothiazole in the form of a white product melting at 80°-82°C.

Analysis: $C_7H_{11}N_2O_4PS_2$; molecular weight = 282.28
Calculated: % C 29.80 % H 3.91 % N 9.91 % P 10.98
Found: 29.8 4.2 9.5 11.1

EXAMPLE 5

3-(diethoxy thiophosphoryloxy)-4-cyano-5-phenyl-isothiazole

STEP A: 3-hydroxy-4-cyano-5-phenyl-isothiazole

A mixture of 20 g of 3-methoxy-4-cyano-5-phenyl-isothiazole [prepared by the method of U.S. Pat. No. 3,476,765] and 200 ml of a solution of 25 parts by weight of hydrobromic acid in 75 parts by weight of acetic acid was heated at 80°C with stirring for 1 hour and the resulting suspension was evaporated to dryness under reduced pressure. The residue was empasted with ethanol and the mixture was vacuum filtered to obtain 16 g of 3-hydroxy-4-cyano-5-phenyl-isothiazole in the form of white crystals melting at 234°C.

STEP B: 3-(diethoxy thiophosphoryloxy)-4-cyano-5-phenyl-isothiazole 5 g of sodium hydride as a 50% suspension in mineral oil were added with stirring to a solution of 24.2 g of 3-hydroxy-4-cyano-5-phenyl-isothiazole in 250 ml of dimethylformamide and then 22.5 g of 0,0-diethyl chlorothiophosphate were added thereto. The mixture stood for 3 hours at room temperature and was then poured over ice. The mixture was extracted with isopropyl ether and the organic phase was dried over sodium sulfate and evaporated to dryness to obtain 42 g of an oil. The oil was chromatographed over silica gel and the eluant was 2-8 ethyl acetate-cyclohexane mixture to obtain 28.5 g of 3-(diethoxy thiophosphoryloxy)-4-cyano-5-phenyl-isothiazole in the form of a clear yellow oil with a refractive index of $n_D^{20} = 1.5815$.

Analysis: $C_{14}H_{15}N_2O_3PS_2$; molecular weight = 354.40
Calculated: % C 47.45 % H 4.26 %N 7.91 %P 8.75
Found: 47.8 4.3 7.5 8.6

EXAMPLE 6

3-(dimethoxy thiophosphoryloxy)-4-cyano-5-phenyl-isothiazole

A mixture of 3.2 g of sodium hydride as a 50% suspension in a mineral oil in a solution of 13 g of 3-hydroxy-4-cyano-5-phenyl-isothiazole in 150 ml of dimethylformamide was stirred for 1 hour at room temperature and then 9.6 g of 0,0-dimethyl chlorothiophosphate were added thereto. The mixture was stirred for 1 hour and then poured into ice water. The mixture was extracted with ether and the organic phase was dried over magnesium sulfate and evaporated to dryness to obtain 20 g of an oil which was chromatographed over silica gel and the eluant was benzene to obtain 12.1 g of 3-(dimethoxy thiophosphoryloxy)-4-cyano-5-phenyl-isothiazole in the form of white crystals melting at about 40°C. A sample for microanalysis was crystallized from an 8-2 hexane- isopropyl ether mixture and melted at 40°C.

Analysis: $C_{12}H_{11}N_2O_3PS_2$; molecular weight = 326.35
Calculated: % C 44.17 % H 3.40 %N 8.58 % P 9.50
Found: 44.0 3.4 8.4 9.2

EXAMPLE 7

3-(dimethoxy thiophosphoryloxy)-4-cyano-5-n-butyl-thiazole

STEP A: Ethyl imino valerate hydrochloride

A current of gaseous hydrochloric acid was passed for 6 hours at 0°C through a mixture of 85 g of valeronitrile, 1000 ml of ethyl ether and 63 g of ethylmercaptan and the mixture was then evaporated to dryness to obtain 176 g of ethyl iminovalerate hydrochloride melting at 40°-50°C.

STEP B: Ethyl dithiovalerate

A current of hydrogen sulfide was passed for 1 hour at 0°C through 2000 ml of pyridine and then 172 g of the product of Step A were added thereto. The current of hydrogen sulfide was bubbled therethrough for 4 hours and the mixture was added to an ice-water mixture. The mixture was acidified to a pH of 2 with hydrochloric acid and was extracted with ether. The extracts were dried and evaporated to dryness to obtain 145 g of ethyl dithiovalerate in the form of a yellow oil with a boiling point of 71°C at 5 mm Hg.

STEP C: Potassium 3-mercapto-2-cyano-2-heptenonitrile 13.2 g of malonitrile were added to a mixture of 14 g of potassium methylate in 300 ml of methanol and then 35 g of ethyl dithiovalerate were added thereto. The mixture was stirred for 18 hours and then was evaporated to dryness to obtain 41 g of potassium 3-mercapto-2-cyano-2-heptenonitrile in the form of a viscous oil.

STEP D: 3-hydroxy-4-cyano-5-n-butyl-isothiazole 25 ml of 110 volume hydrogen peroxide were added to a solution of 41 g of potassium 3-mercapto-2-cyano-2-heptenonitrile in 300 ml of water and the mixture was stirred for 1 hour at 20°C. The mixture was washed with ethyl acetate, acidified with hydrochloric acid and extracted with ethyl acetate. The ethyl acetate phase was dried and evaporated to dryness. The crystals resulting were washed with petroleum ether (B.p. = 35°–70°C) and dried to obtain 28 g of 3-hydroxy-4-cyano-5-n-butyl-thiazole melting at 118°–120°C.

STEP E: 3-(dimethoxy thiophosphoryloxy)-4-cyano-5-n-butyl-isothiazole

A mixture of 6.4 g of 0,0-dimethyl chlorothiophosphate, 7.6 g of 3-hydroxy-4-cyano-5-n-butyl-isothiazole, 50 ml of acetone and 5.6 g of potassium carbonate was stirred for 18 hours and then filtered. The filtrate was evaporated to dryness and the residue was chromatographed over silica gel. Elution with a 9-1 cyclohexane-ethyl acetate mixture resulted in 9.6 g of 3-(dimethoxy-thiophosphoryloxy)-4-cyano-5-n-butyl-isothiazole in the form of an oil.

Analysis: $C_{10}H_{15}N_2O_3PS_2$; molecular weight = 306.35
Calculated: % C 39.20 % H 4.94 % N 9.14 % P 10.11
Found: 39.8 5.0 9.1 9.8

EXAMPLE 8

3-(dimethoxy thiophosphoryloxy)-4-ethoxycarbonyl-5-methyl-isothiazole

STEP A: 3-hydroxy-4-ethoxycarbonyl-5-methyl-isothiazole 320 ml of a 47°Be potassium hypochlorite solution were added dropwise at 0°C to a mixture of 82 g of the potassium salt of ethyl 2-mercapto-2-methyl-1-ethoxycarbonylacrylate [Hartke et al, Arch. Pharm., Vol. 301 (1968), p. 601] and 500 ml of 22°Be ammonium hydroxide and after stirring for 3 hours at 0°C, the mixture was vacuum filtered. The precipitate recovered was added to a mixture of 160 ml of methylene chloride and 160 ml of water and 19 ml of concentrated hydrochloric acid were added thereto. The mixture was stirred for 1 hour and the organic phase was decanted, dried over magnesium sulfate and evaporated to dryness to obtain 38.5 g of 3-hydroxy-4-ethoxycarbonyl-5-methyl-isothiazole melting at 69°C and thin-layer chromatography: Rf = 0.5 (silica; 7–3 benzene-ethyl acetate).

STEP B: 3-(dimethoxy thiophosphoryloxy)-4-ethoxycarbonyl-5-methyl-isothiazole

A mixture of 10 g of 3-hydroxy-4-ethoxycarbonyl-5-methyl-isothiazole, 13 g of 0,0-dimethylchlorothiophosphate, 11.3 g of potassium carbonate and 200 ml of acetone was stirred for 24 hours at room temperature and was filtered. The filtrate was evaporated to dryness under reduced pressure and the residue was chromatographed over silica. Elution with 9-1 benzene-ethyl acetate resulted in 4.2 g of 3-(dimethoxy thiophosphoryloxy)-4-ethoxycarbonyl-5-methyl-isothiazole in the form of a yellow oil with a refractive index of $n_D^{20} = 1.5307$.

Analysis: $C_9H_{14}NO_5PS_2$; molecular weight = 311.32
Calculated: % C 34.73 % H 4.53 % N 4.5 % P 9.95
Found: 35.1 4.7 4.5 9.8

EXAMPLE 9

3-(diethoxy thiophosphoryloxy)-4-ethoxycarbonyl-5-methyl-isothiazole

Using the procedure of Example 8, 8 g of 3-hydroxy-4-ethoxycarbonyl-5-methyl-isothiazole and 10.2 g of 0,0-diethyl chlorothiophosphate were reacted and the residue was chromatographed over silica with a 6-4 cyclohexane-ethyl acetate eluant to obtain 4 g of 3-(diethoxy thiophosphoryloxy)-4-ethoxycarbonyl-5-methyl-isothiazole in the form of an oil with a refractive index of $n_D^{18} = 1.5120$ Analysis: $C_{11}H_{18}NO_5PS_2$; molecular weight = 339.37
Calculated: % C 38.93 % H 5.35 % N 4.13 % P 9.13
Found: 39.1 5.6 4.1 9.4

EXAMPLE 10

3-(dimethoxythiophosphoryloxy)-4-methoxycarbonyl-5-methyl-isothiazole

Using the procedure of Step A of Example 8, 3-hydroxy-4-methoxycarbonyl-5-methyl-isothiazole with a melting point of 88°C was prepared. 53. g of the said product and 70 g of 0,0-dimethyl chlorothiophosphate were reacted and chromatography over silica with an 8-2 cyclohexane-ethyl acetate mixture as eluant resulted in 12 g of 3-(dimethoxythiophosphoryloxy)-4-methoxycarbonyl-5-methyl-isothiazole in the form of an oil with a refractive index of $n_D^{22} = 1.5361$ Analysis: $C_8H_{12}NO_5PS_2$; molecular weight = 297.29
Calculated: % C 32.32 % H 4.07 % N 4.72 % P 10.42
Found: 32.7 4.1 4.7 10.0

EXAMPLE 11

3-(dimethoxy phosphoryloxy)-4-methoxycarbonyl-5-methyl-isothiazole

A mixture of 17.2 g of 3-hydroxy-4-methoxycarbonyl-5-methyl-isothiazole, 13.2 g of 0,0-dimethyl chlorophosphate, 10 g of triethylamine and 100 ml of acetonitrile was stirred for 24 hours at room temperature and was concentrated to dryness under reduced pressure. The residue was taken up in benzene and the organic solution was washed with dilute sodium hydroxide and then water, was dried over magnesium sulfate and evaporated to dryness. The residue was chromatographed over silica and was eluted with ethyl acetate to obtain 6 g of 3-(dimethoxy phosphoryloxy)-4-methoxycarbonyl-5-methyl-isothiazole in the form of an oil with a refractive index of $n_D^{22} = 1.5051$ Analysis: $C_8H_{12}NO_6PS$; molecular weight = 281.23
Calculated: % C 34.16 % H 4.40 % N 4.98 % P 11.01
Found: 34.2 4.4 5.0 10.7

Insecticidal study of 3-(diethoxy thiophosphoryloxy)-4-cyano-5-phenyl-isothiazole (A)

A. Test Against *Ceratitis Capitata*

This test was effected by topical application of the test compounds in acetone solutions corresponding to 100 and 1000 mg of active product per liter. 1 μl of the acetone solution was applied to the dorsal thorax of *Ceratitis Capitata* flies aged 2.5 days (+ 0.5) at a rate of 50 flies per dose and per test. The number of flies still living and those dead for the tested compounds were determined at 2 and 24 hours after the test and the percent of mortality was determined. the results are shown in Table I.

TABLE I

| Product | mg/l | % mortality after | |
|---------|------|-------------------|------|
|         |      | 2 hours | 24 hours |
| A       | 1000 | 86.0    | 100      |
|         | 100  | 11.5    | 84.6     |
| DDT     | 100  | 22.4    | 22.4     |

Table I shows that Compound A has a very good insecticidal activity against *Ceratitis Capitata* which was superior to DDT (dichlorodiphenyltrichloroethane).

B. Test Against Sitophilus Granarius

This test was effected by topical application of the test compounds in acetone solution at a rate of 500 mg of active compound per liter. 0.2 μl of the acetone solution was applied to the ventral thorax of *Sitophilus Granarius* of 50 insects per concentration and per test. The number of insects living and dead was determined after 24 and 48 hours and 5 days. The results are reported in Table II.

TABLE II

| Product | mg/l | % mortality after | | |
|---------|------|-----|-----|-----|
|         |      | 24 hours | 48 hours | 5 days |
| A       | 500  | 14.2 | 16.3 | 40.7 |
| Malathion | 500 | 2.0 | 2.0 | 20.0 |

Table II shows that Compound A has an insecticidal activity in this test superior to Malathion (0,0-dimethyl phosphorodithioate of ethyl mercaptosuccinate).

C. Test Against Adult *Musca Domestica*

This test consisted of a topical application of a microliter of an acetone solution of the test compound to the dorsal thorax of flies after having been put to sleep with ether. The insects were held at 20°C at 50% relative humidity and were fed with milk or water. The results were determined 24 hours after treatment of determine the percentage of mortality for 3-(dimethoxy thiophosphoryloxy)-4-ethoxycarbonyl-5-methyl-isothiazole (Compound B) and 3-(diethoxy thiophosphoryloxy)-4-ethoxycarbonyl-5-methyl-isothiazole (Compound C) and the results are reported in Table III.

TABLE III

| Product | mg/l | % mortality after 24 hr. |
|---------|------|--------------------------|
| B       | 2500 | 100 |
|         | 500  | 100 |
| C       | 2500 | 100 |
|         | 500  | 36  |

Products B and C have a very great insecticidal activity against adult Musca Domestica.

D. Test on Musca Domestica Larvae

This contact-ingestion test consisted of placing 2 ml of an acetone solution of differing concentrations of the test compound with 1 g of bran on a watch glass.

The solvent was evaporated and the treated bran was placed in a box made of plastic material and 2 ml of milk were added. After a good mixing, the mixture was contaminated with 20 larvae of *Musca domestica* 3 to 4 days old. Three tests were run for each concentration and the larvae were held at 20°C and 30% relative humidity. The results wee determined 48 hours and 8 days after treatment and the percent of mortality was reported in Table IV.

TABLE IV

| Product | mg/l | % mortality after | |
|---|---|---|---|
| | | 48 hours | 8 days |
| B | 5000 | 67 | 98 |
| | 500 | 28 | 91 |
| C | 5000 | 57 | 98 |
| | 500 | 31 | 81 |

Products B and C have a very good insecticidal activity against *Musca domestica* larvae equal to Carbaryl (1-naphthyl-methyl-carbamate).

E. Test Against Sitophilus Granarius

This test was effected by topical application of the test compounds in acetone solution at a rate of 500 mg of active compound per liter. 0.2 μl of the acetone solution was applied to the ventral thorax of *Sitophilus granarius* of 50 insects per concentration and per test. The number of insects living and dead was determined after 24 hours, 48 hours and 5 days. The results are reported in Table V.

TABLE V

| Product | mg/l | % mortality | | |
|---|---|---|---|---|
| | | 24 hr. | 48 hr. | 5 days |
| B | 500 | 100 | 100 | 100 |
| | 50 | 51 | 68 | 89 |

Product B has a very good insecticidal activity against *Sitophilus granarius*.

EXAMPLE A

A mixture consisting of 25% by weight of compound A, 6.4% by weight of Atlox 4851 (mixture of alkylarylsulfonate and polyoxyethylene triglyceride with a viscosity of 300 to 700 cps at 25°C), 3.2% by weight of Atlox 4855 (mixture of alkylarylsulfonate and polyoxyethylene triglycerides with a viscosity of 1500 to 1900 cps at 25°C) and 65.4% by weight of xylene were intimately admixed to obtain a homogeneous liquid composition. The concentrate could be mixed with varying amounts of water depending upon the desired dose.

EXAMPLE B

A mixture consisting of 15% by weight of 3-(dimethoxythiophosphoryloxy)-4-ethoxycarbonyl-5-methyl-isothiazole, 6.4% by weight of Atlox 4851, 3.2% by weight of Atlox 4855 and 75.4% by weight of xylene were intimately admixed to obtain a homogeneous liquid composition suitable for use as an insecticide or acaricide.

Various modifications of the compositions and methods of the invention may be made without departing from the spirit or scope thereof and it should be understood that the invention is to be limited only as defined in the appended claims.

We claim:

1. A compound of the formula

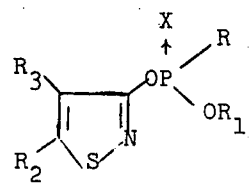

wherein R is selected from the group consisting of alkyl of 1 to 3 carbon atoms, alkoxy of 1 to 3 carbon atoms and

R' and R" being individually selected from the group consisting of hydrogen and alkyl of 1 to 3 carbon atoms, $R_1$ is alkyl of 1 to 3 carbon atoms, $R_2$ is selected from the group consisting of hydrogen, alkyl of 1 to 5 carbon atoms, aryl of 6 to 10 carbon atoms, aralkyl of 7 to 12 carbon atoms, cyano, carbalkoxy of 2 to 4 carbon atoms and NHR''', R''' is selected from the group consisting of hydrogen and aryl of 6 to 10 carbon atoms, $R_3$ is selected from the group consisting of cyano, alkylthio of 1 to 4 carbon atoms, alkylsulfinyl of 1 to 4 carbon atoms, alkylsulfonyl of 1 to 4 carbon atoms, carbamoyl, carbalkoxy of 2 to 4 carbon atoms and

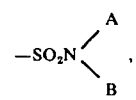

A and B are individually selected from the group consisting of hydrogen and alkyl of 1 to 3 carbon atoms and X is selected from the group consisting of oxygen and sulfur.

2. A compound of claim 1 wherein $R_2$ is selected from the group consisting of hydrogen, alkyl of 1 to 3 carbon atoms, aryl of 6 to 10 carbon atoms, aralkyl of 7 to 12 carbon atoms, cyano, carbalkoxy of 2 to 4 carbon atoms and NHR''' and R''' is selected from the group consisting of hydrogen and aryl of 6 to 10 carbon atoms.

3. A compound of claim 1 which is 3-(diethoxythiophosphoryloxy)-4-cyano-5-methyl-isothiazole.

4. A compound of claim 1 which is 3-(dimethoxythiophosphoryloxy)-4-cyano-5-methyl-isothiazole.

5. A compound of claim 1 which is 3-(diethoxythiophosphoryloxy)-4-carbamoyl-5-methyl-isothiazole.

6. A compound of claim 1 which is 3-(dimethoxythiophosphoryloxy)-4-carbamoyl-5-methyl-isothiazole.

7. A compound of claim 1 which is 3-(diethoxythiophosphoryloxy)-4-cyano-5-phenyl-isothiazole.

8. A compound of claim 1 which is 3-(dimethoxythiophosphoryloxy)-4-cyano-5-phenyl-isothiazole.

9. A compound of claim 1 which is 3-(dimethoxythiophosphoryloxy)-4-cyano-5-n-butyl-isothiazole.

10. A compound of claim 1 which is 3-(dimethoxythiophosphoryloxy)-4-ethoxycarbonyl-5-methyl-isothiazole.

11. A compound of claim 1 which is 3-(diethoxythiophosphoryloxy)-4-ethoxycarbonyl-5-methyl-isothiazole.

12. A compound of claim 1 which is 3-(dimethoxythiophosphoryloxy)-4-methoxycarbonyl-5-methyl-isothiazole.

13. A compound of claim 1 which is 3-(dimethoxy phosphoryloxy)-4-methoxycarbonyl-5-methyl-isothiazole.

* * * * *